United States Patent [19]
Mattox

[11] Patent Number: 5,869,510
[45] Date of Patent: Feb. 9, 1999

[54] IRON STABILIZERS FOR 3-ISOTHIAZOLONES

[75] Inventor: John Robert Mattox, Perkasie, Pa.

[73] Assignee: Rohm and Haas Company, Philadelphia, Pa.

[21] Appl. No.: 6,021

[22] Filed: Jan. 15, 1993

[51] Int. Cl.$^6$ .................. A01N 43/80; C07D 275/02; C07D 277/02
[52] U.S. Cl. ............................ 514/372; 548/213
[58] Field of Search .............. 548/213; 514/372

[56] References Cited

U.S. PATENT DOCUMENTS

| | | | |
|---|---|---|---|
| 3,870,795 | 3/1975 | Miller et al. | 548/213 |
| 4,031,055 | 6/1977 | Dupont et al. | 260/29 |
| 4,067,878 | 1/1978 | Miller et al. | 548/213 |
| 4,150,026 | 4/1979 | Miller et al. | 548/213 |
| 4,310,590 | 1/1982 | Petigara | 548/213 |
| 5,118,699 | 6/1992 | Willingham et al. | 548/213 |
| 5,142,058 | 8/1992 | Willingham et al. | 548/213 |
| 5,145,981 | 9/1992 | Willingham | 548/213 |
| 5,153,213 | 10/1992 | Schmidt | 514/372 |
| 5,160,527 | 11/1992 | Law et al. | 548/213 |

FOREIGN PATENT DOCUMENTS

| | | |
|---|---|---|
| 425143 | 10/1990 | European Pat. Off. . |
| 399724 | 11/1990 | European Pat. Off. . |
| 457435 | 11/1991 | European Pat. Off. . |
| 2200846 | 8/1988 | United Kingdom . |

OTHER PUBLICATIONS

Chemical Abstract, vol. 98 No. 3, p. 307, column 1, The effects of metals upon the inhibitory activities of cutting fluid preservatives., EO Bennett et al. (1983).

Database WPI, Derwent Publications, JP A 60 042 306, abstract, Tokyo Org. Chem. Ind. (Mar. 6, 1985).

*Primary Examiner*—Johann Richter
*Assistant Examiner*—Jane C. Osweckі
*Attorney, Agent, or Firm*—S. Matthew Cairns; Michael B. Fein

[57] ABSTRACT

A method paring a stable, dilute aqueous solution of at least one 3-isothiazolone compound comprising 5-chloro-2-methyl-3-isothiazolone, the concentration of said compound (s) in said solution being about 0.5 to 5% by weight based on solution, comprising introducing about 0.1 to 5% by weight based on said solution, of a ferric salt as the stabilizer is disclosed. Dilute aqueous solutions of about 0.5 to 5.0 parts by weight of at least one 3-isothiazolone compound comprising 5-chloro-2-methyl-3-isothiazolone, about 0.1 to 2.5 parts by weight of a stabilizing, water soluble, non-chelated ferric salt, and about 92 to 99 parts by weight of aqueous solvent, are also disclosed.

7 Claims, No Drawings

IRON STABILIZERS FOR 3-ISOTHIAZOLONES

BACKGROUND OF THE INVENTION

1. Field of the Invention

This invention relates to stabilization of 3-isothiazolone compounds present in the form of dilute aqueous solutions.

2. Description of the Prior Art

3-Isothiazolone compounds (hereafter "active ingredient" or AI) are a very important class of microbicides. Several species have been commercialized and are widely used to inhibit the growth of bacteria, fungi and algae. Among the most important species are 2-methyl-3-isothiazolone ("MI"), 5-chloro-2-methyl-3-isothiazolone ("CMI"), and especially mixtures thereof. A 3/1 weight ratio mixture of CMI and MI is used in a wide variety of commercial applications around the world. CMI is naturally unstable and much research has been devoted to stabilizing it in four separate classes of environments: (1) the isolated compound itself; (2) "concentrates" which are about 14 to 25% by weight aqueous solutions of the AI; (3) "dilute solutions" which are about 1 to 5% by weight aqueous solutions of the AI and which are designed to be diluted further when added to a locus; and (4) "use dilutions" which are the end use dilution in the locus to be protected and comprise substantially less than 1% by weight AI.

To stabilize the isolated compound (1), U.S. Pat. No. 4,150,026 teaches making metal salt complexes of isothiazolones. These complexes are taught to greatly enhance the thermal stability of solid isothiazolones, compared to the corresponding uncomplexed isothiazolones. No mention is made regarding the stabilization of aqueous solutions of isothiazolones, i. e., (2) or (3), or the use dilutions (4), against chemical decomposition of the AI.

U.S. Pat. No. 3,870,795 teaches the stabilization of 3-isothiazolone concentrates, i.e., (2), against chemical decomposition by addition of metal nitrite or metal nitrate. Among the useful nitrates are taught those of sodium, potassium, calcium, magnesium, ferric, ferrous, nickel, zinc, barium, manganese, silver, cobalt, and the like, and among the useful nitrites are taught those of sodium, potassium, calcium, magnesium, and the like. The '795 patent discloses that other common anions, including carbonates, sulfates, chlorates, perchlorates, and chlorides, are surprisingly ineffective. The '795 patent also teaches that the isothiazolone can be an aqueous solution of the compound itself, or of the complexes. According to '795, neither the concentrates, nor the complexes, nor non-aqueous 25% by weight solutions of either the compounds or the complexes, are stable unless stabilized with nitrates or nitrites. This patent does not teach stabilization of dilute solutions (3). All of the '795 examples are directed to 25% solutions of the compounds or the complexes thereof. The concentrates are thus taught by the prior art to be stabilized by nitrates or nitrites, irrespective of the metal counter ion, and the present invention is not inconsistent.

Commercial concentrates (2) contain 3:1 mixtures of CMI and MI as the active ingredient and magnesium nitrate stabilizer in an approximate 1:1 weight ratio of stabilizer to AI. Magnesium chloride is also present as a by-product of the neutralization step in the preparation of the isothiazolone.

To stabilize the AI in use dilutions (4), Law et al., U.S. Pat. No. 5,160,527 suggest metal salts (Cu, ferrous, ferric, zinc, manganese, magnesium) of an organic carboxylic acid of at least six carbon atoms, (which are water insoluble) or chelating anions selected from EDTA, 8-hydroxy-5-hydroxyquinolinate, gluconate, o-phenanthroline, quinolinate, N,N-bis(2-hydroxy-5-sulfobenzyl)glycine, lignosulfonate polymers, and polyacrylates. The use dilutions suggested by Law, et al., comprise loci which contain destabilizing components such as amines, reducing agents (e.g., bisulfites), and fuel. These "destabilizing components" react with the AI. Law et al. do not teach any method of stabilizing dilute solutions which consist of the AI and aqueous solvent in the absence of the aforementioned destabilizing components.

Willingham, et al., U.S. Pat. No. 5,118,699, teaches the stabilizing effect of hydrazide compounds for isothiazolones present in metal working fluids and similar loci containing components antagonistic to the AI. Willingham, et al., U.S. Pat. No. 5,142,058, teaches the stabilizing effect of alkyl halohydantoins and the like in similar antagonistic loci, i.e., use dilutions. These Willingham, et al., patents do not relate to stability in dilute solutions.

For dilute solutions (3), there are two conventional methods of stabilization. The first is to use high ratios (e.g., about 15:1) of $Mg(NO_3)_2$ to AI. $Mg(NO_3)_2$ is not effective at lower ratios, i.e., about 1:1. The second is to use a cupric salt as the stabilizer. The cupric salt is conventionally used at a ratio of about 1:10 to AI since only very small amounts of cupric ion are necessary for effective stabilization. The reason use of cupric ion is preferred in industrial situations is that too much nitrate salt is disadvantageous in certain applications or loci.

However, the cupric stabilizer has recently come under question because of government regulatory limits in certain countries on the amount permitted in water discharge streams.

Since dilute solutions have certain advantages over the concentrates (ease of handling, reduced potential for sensitization of workers, and greater flexibility of formulations), it became necessary to find an alternative stabilization method to the cupric ion or high levels of nitrates.

SUMMARY OF THE INVENTION

It is an object of the invention to provide a stabilization system for dilute solutions of chlorinated 3-isothiazolone compounds which is effective and yet avoids the need for copper or high levels of nitrates.

This object, and others which will become apparent from the following disclosure, are achieved by the present invention which comprises in one aspect a method of stabilizing a dilute solution of at least one 3-isothiazolone compound comprising 5-chloro-2-methyl-3-isothiazolone, the concentration of said 3-isothiazolone compound(s) in said dilute solution being about 0.5 to 5% by weight based on said dilute solution, comprising introducing about 0.1 to 5% by weight based on said dilute solution, of a ferric salt.

In another aspect, the invention comprises a composition comprising a dilute solution of about 0.5 to 5.0 parts by weight of at least one 3-isothiazolone compound comprising 5-chloro-2-methyl-3-isothiazolone, 0.1 to 2.5parts by weight of a stabilizing, water soluble, non-chelated ferric salt, and about 92 to 99 parts by weight of aqueous solvent.

DETAILED DESCRIPTION AND THE PREFERRED EMBODIMENTS

Any normally unstable, water soluble 3-isothiazolone compound can be stabilized according to this invention. The invention is especially useful for CMI, either as a sole compound or in admixture with MI.

Preferred compositions are dilute solutions which comprise about 0.5 to about 5% by weight, preferably about 1–5% by weight, of one or more isothiazolone compounds dissolved in aqueous solvent and a stabilizing amount of a ferric salt in the range of from about 0.05 to about 10%, preferably 0.25 to 1% by weight, based on the dilute solution.

In preparing the dilute solutions of the invention, the aqueous solvent can comprise certain organic solvents, in addition to water, although only at relatively low levels. Suitable organic solvents are ethylene glycol, diethylene glycol, diethylene glycol butyl ether, propylene glycol, dipropylene glycol, dipropylene glycol butyl ether, polypropylene glycol, polyethylene glycol, methoxy ethanol, and the like, and the amounts used can be up to 30% by weight based on the dilute solution. The preferred solvent is all water and no organic solvent.

The ferric salts useful in this invention are those which are soluble in the aqueous solvent used and function to stabilize the AI in the dilute aqueous solutions. The preferred ferric salts are consisting of ferric chloride, ferric nitrate, ferric sulfate, ferric bromide, ferric acetate, and ferric iodide. Because of handling and economics, ferric sulfate is preferred.

It has been surprisingly found that it is possible to extend the stabilizing effect of low levels of ferric ion by the addition of small amounts of an oxidant. Suitable oxidants are sodium chlorate (which is preferred) and N-bromosuccinimide. The amount of oxidant used is preferably about 0.1% to about 5.0% by weight, more preferably about 0.5% to about 1.5% by weight, based on dilute solution. When slightly higher levels of ferric salt are used, use of the oxidant is not necessary or preferred.

It is also preferred to add a small amount of acid to prevent precipitate formation. The acid does not negatively affect the stabilizing action of the ferric salt, and is compatible with the isothiazolone. Any acid which effectively lowers the pH of the stabilized isothiazolone solution may be used. Preferred acids are hydrochloric acid, nitric acid, and sulfuric acid. The amount of acid required will vary depending upon the initial pH of the stabilized isothiazolone solution and the proposed end use of the isothiazolone, among other factors, but will generally be used in an amount sufficient to lower the pH of the stabilized isothiazolone solution to at least about 1.5. The preferred acid is hydrochloric.

The dilute solutions of the invention can be prepared from concentrates by adding water and ferric salt. Typical concentrates comprise about 14% AI and 14% $Mg(NO_3)_2$ in an aqueous solution. The dilutions can also be prepared by dilution with aqueous solvent of a salt free, i.e., $MgNO_3$-free, solution of AI in a glycol. The dilute solutions can also be prepared directly from salt-free technical AI, aqueous solvent, and ferric salt.

The compositions of this invention are suitable for a wide variety of applications in a number of industries. The dilute solutions are further diluted when introduced into, onto, or at a locus to be protected. The loci in which the use dilutions are particularly useful are water treatment, especially in pulp and paper processing and in cooling towers. Other examples of loci are adhesives, sealants, agriculture adjuvant preservation, construction products, cosmetics and toiletries, disinfectants and antiseptics, emulsions and dispersions, formulated consumer and industrial products, industrial processing, laundry, leather and leather products, lubricants and hydraulic aids, medical devices, metalworking and related applications, odor control, paints and coatings, petroleum refining and fuels, photographic chemicals, printing, sanitizers, soaps and detergents, textiles and textile products and textile processing, water purification and wood applications. The ferric ion which stabilizes the AI in the dilute solutions according to the present invention does not function to stabilize AI in the loci (i.e., in used dilutions) when diluted an introduced in these loci. Other stabilizers are needed in certain of these loci, especially metal working fluids, shampoos, caulks, paints, other latices, and the like.

It is known in the art that the performance of microbicides may be enhanced by combination with one or more other microbicides. Thus, other known microbicides may be combined advantageously with the composition of this invention.

The following specific examples are presented to illustrate various aspects of the invention but are not to be construed as limitations thereof. All parts and percentages are by weight unless otherwise specified, and all reagents are of good commercial quality unless otherwise specified. The relative concentration of the active ingredient was determined by reverse phase high performance liquid chromatography (HPLC), utilizing an ultraviolet detector, unless otherwise noted. Adequate stabilization was defined as 60% of the isothiazolone remaining after 4 weeks at 55° C.

EXAMPLE 1 (Comparative)

This example illustrates the effect of increasing dilutions with water of a "concentrate," i.e., an aqueous solution containing 25% isothiazolone and 25% magnesium nitrate stabilizer. The isothiazolone was a 3:1 by weight mixture of CMI and MI. The dilutions shown in Table 1 were prepared and stored at 55° C. for 8 weeks and analyzed for CMI at the time intervals of 1, 2, 3, 4, 6, and 8 weeks.

TABLE 1

| | | % CMI Remaining Weeks | | | | | |
|---|---|---|---|---|---|---|---|
| % AI | % Stabilizer | 1 | 2 | 3 | 4 | 6 | 8 |
| 25 | 25 | 93 | 86 | 76 | 61 | 0 | — |
| 12 | 12 | 84 | 74 | 61 | 45 | 0 | — |
| 6 | 6 | 77 | 66 | 51 | 33 | 0 | — |
| 3 | 3 | 55 | 38 | 21 | 7 | 0 | — |
| 1.5 | 1.5 | 31 | 0 | — | — | — | — |

These data indicate that conventional magnesium nitrate stabilizer, used at a 1/1 weight ratio to 3-isothiazolone, becomes less effective with increasing dilution with water.

EXAMPLE 2 (Comparative)

Stabilizing Effect of Salts of Various Metal Ions

Dilute solutions (1.5% CMI/MI, 3:1) with 1% of various metal salts in water were prepared and evaluated for stabilization of the active ingredient. The samples were stored at 55° C for 2 weeks. Analyses were performed at the time of preparation and after storage using a UV absorption method. The results are reported as percent AI lost.

TABLE 2

| Stabilizer | % Isothiazolone Lost |
| --- | --- |
| None (−control) | 82 |
| Cupric nitrate (+control) | 0 |
| Ferric sulfate (Invention) | 0 |
| Ferrous sulfate (Comparative) | 74 |
| Zinc sulfate (Comparative) | 82 |
| Zirconium sulfate (Comparative) | 79 |
| Chromium nitrate (Comparative) | 73 |
| Cerium (IV) sulfate (Comparative) | 69 |
| Cobalt sulfate (Comparative) | 77 |
| Nickel sulfate (Comparative) | 77 |
| Manganese sulfate (Comparative) | 85 |
| Lead nitrate (Comparative) | 64 |
| Lanthanum sulfate (Comparative) | 84 |
| Thorium sulfate (Comparative) | 74 |
| Tin (II) chloride (Comparative) | 97 |
| Bismuth tartrate (Comparative) | 78 |

This example demonstrates that ferric ion is exceptional in that it functions as an effective stabilizer of dilute solutions when added at a 1% based on weight of solution, whereas other metals, except for copper, do not. This example also demonstrates that nitrate ion when added at 1% based on weight of solution is not effective as a stabilizer in dilute solutions, either, except when used as a counterion with ferric or cupric cations.

EXAMPLE 3 (Comparative)

This example demonstrates the unusual effectiveness of ferric cation as a stabilizer of AI in dilute solutions compared to other cations disclosed as stabilizers for concentrates in the '795 patent. In this example, nitrates of the various cations were compared at 1.5% concentration in water solutions containing about 1.5% AI. The % CMI remaining after 1 and 2 weeks was measured and reported in Table 3.

TABLE 3

Stability of Dilute Solutions of AI Containing Metal Nitrate Salts

| | | | Chemical Stability | | |
| --- | --- | --- | --- | --- | --- |
| Invention/ Comparative | Stabilizer (1.5%, anhyd) | Wks (55° C.) | % MI | % CMI | % CMI remaining |
| Invention | Fe(NO$_3$)$_3$ | 0 | 0.41 | 1.32 | 100 |
| | | 1 | 0.41 | 1.32 | 100 |
| | | 2 | 0.41 | 1.33 | 100 |
| | | 4 | 0.42 | 1.34 | 100 |
| Comparative | Mg(NO$_3$)$_2$ | 0 | 0.35 | 1.15 | 100 |
| | | 1 | 0.34 | 0.73 | 63 |
| | | 2 | 0.34 | 0.72 | 63 |
| | | 4 | 0.31 | 0.44 | 38 |
| Comparative | Ni(NO$_3$)$_2$ | 0 | 0.35 | 1.10 | 100 |
| | | 1 | 0.36 | 0.69 | 63 |
| | | 2 | 0.35 | 0.68 | 62 |
| | | 4 | 0.33 | 0.44 | 40 |
| Comparative | Zn(NO$_3$)$_2$ | 0 | 0.35 | 1.15 | 100 |
| | | 1 | 0.35 | 0.67 | 58 |
| | | 2 | 0.34 | 0.66 | 57 |
| | | 4 | 0.32 | 0.44 | 38 |
| Comparative | Mn(NO$_3$)$_2$ | 0 | 0.32 | 1.03 | 100 |
| | | 1 | 0.32 | 0.74 | 72 |
| | | 2 | 0.32 | 0.73 | 71 |
| | | 4 | 0.28 | 0.46 | 45 |
| Comparative | NaNO$_3$ | 0 | 0.38 | 1.22 | 100 |
| | | 1 | 0.37 | 0.75 | 61 |
| | | 2 | 0.36 | 0.74 | 61 |
| | | 4 | 0.33 | 0.46 | 38 |
| Comparative | Ca(NO$_3$)$_2$ | 0 | 0.38 | 1.23 | 100 |
| | | 1 | 0.37 | 0.80 | 65 |
| | | 2 | 0.36 | 0.80 | 65 |
| | | 4 | 0.35 | 0.49 | 40 |
| Control (−) | no stabilizer | 0 | 0.35 | 1.14 | 100 |
| | | 1 | 0.23 | 0.00 | 0 |
| | | 2 | 0.23 | 0.00 | 0 |
| | | 4 | 0.17 | 0 | 0 |

EXAMPLE 4

The effect of varying the anion of the soluble ferric salt as well as the concentration of the salt was determined. A series of 1.5% isothiazolone (3:1 mixture CMI and MI) dilute solutions was prepared by diluting a concentrate based on 14% of the 3:1 mixture of CMI and MI containing 15% Mg(NO$_3$)$_2$ stabilizer. The resultant dilute solution samples were stabilized by the addition of varying amounts of the ferric salts listed in Table 4. The results are shown, in Table 4.

TABLE 4

| | | % CMI Remaining Weeks | | | |
| --- | --- | --- | --- | --- | --- |
| % | Stabilizer | 1 | 3 | 5 | 8 |
| | Control (negative) | 92 | 59 | 30 | — |
| 0.01 | Ferric Chloride | 100 | 81 | 48 | 15 |
| 0.05 | Ferric Chloride | 100 | 96 | 87 | 75 |
| 0.10 | Ferric Chloride | 100 | 100 | 100 | 100 |
| 0.15 | Ferric Chloride | 100 | 97 | 94 | 91 |
| 0.20 | Ferric Chloride | 100 | 97 | 96 | 93 |
| 0.25 | Ferric Chloride | 100 | 96 | 92 | 92 |
| 0.01 | Ferric Nitrate | 100 | 78 | 44 | 13 |
| 0.05 | Ferric Nitrate | 99 | 95 | 80 | 56 |
| 0.10 | Ferric Nitrate | 100 | 97 | 86 | 71 |
| 0.15 | Ferric Nitrate | 100 | 98 | 90 | 80 |
| 0.20 | Ferric Nitrate | 100 | 97 | 92 | 87 |
| 0.25 | Ferric Nitrate | 100 | 100 | 96 | 95 |
| 0.01 | Ferric Sulfate | 100 | 78 | 42 | 9 |
| 0.05 | Ferric Sulfate | 100 | 94 | 74 | 47 |
| 0.10 | Ferric Sulfate | 100 | 90 | 75 | 59 |
| 0.15 | Ferric Sulfate | 100 | 95 | 84 | 75 |
| 0.20 | Ferric Sulfate | 100 | 97 | 88 | 77 |
| 0.25 | Ferric Sulfate | 100 | 98 | 96 | 100 |

These data show that ferric cation is an effective stabilizer at very low concentrations, regardless of the anion.

EXAMPLE 5

In the ferric salt-containing samples of the previous examples, a reddish-brown precipitate was observed after a few weeks storage at 55° C. While this precipitate represents a small amount of material, and in no way interferes with the stabilizing action of the ferric ion, the presence of precipitate is generally considered a negative by commercial users of biocide formulations. The precipitate was found to result from hydrolysis of hydrated ferric ion. Such precipitates can be observed to form upon high temperature storage of aqueous solutions of ferric salts in the absence of isothiazolones.

Dilute solutions of 1.5% isothiazolone were prepared by dilution with water of commercial 14% isothiazolone concentrates which had been stabilized with 15% magnesium nitrate. Ferric chloride (0.25%) was added to stabilize samples A and B. A sample (C) without added ferric chloride served as the control. In sample A the pH was lowered with HCl. A (−) indicates sample is clear and free from precipitate. A (+) indicates sample has a red-brown precipitate. A (*) indicates yellow precipitate as result of AI decomposition.

TABLE 5

Effect of pH Adjustment

| Sample | | Weeks Stored at 55° C. | | | |
|---|---|---|---|---|---|
| | | 0 | 2 | 4 | 8 |
| A | Appearance | − | − | − | − |
| (Adjusted) | pH | 1.0 | 0.8 | 0.8 | 0.7 |
| | % CMI Remaining | 100 | 95 | 94 | 92 |
| B | Appearance | + | + | + | + |
| (Not Adjusted) | pH | 1.5 | 1.0 | 1.2 | 1.2 |
| | % CMI Remaining | 100 | 97 | 96 | 94 |
| C | Appearance | + | + | * | * |
| (Control) | pH | 1.5 | 1.3 | 1.5 | 1.4 |
| | % CMI Remaining | 100 | 79 | 60 | 0 |

These data show that the formation of the red-brown precipitate is prevented by acidifying dilute solutions containing ferric ion stabilizer.

EXAMPLE 6

This example illustrates the use of small amounts of an oxidant to enhance the stabilizing action of ferric ion, thereby allowing use of extremely low levels of ferric salt.

To a 1.5% isothiazolone dilute solution (CMI/MI, 3:1 mixture) was added either 1% sodium chlorate, 0.1% ferric sulfate, or 0.1% ferric sulfate and 1% sodium chlorate. The positive control was commercially available 1.5% isothiazolone dilute solution with added copper as a stabilizer. The negative control was 1.5% AI dilute solution without any added stabilizer. The results are reported in Table 6 as percent CMI remaining.

TABLE 6

| | % CMI Remaining | | | |
|---|---|---|---|---|
| | Weeks | | | |
| | 1 | 2 | 5 | 6 |
| Control (positive) | 100 | 97 | 86 | 88 |
| Control (negative) | 0 | — | — | — |
| 1% NaClO$_3$ | 0 | — | — | — |
| 0.1% Fe$_2$(SO$_4$)$_3$ | 99 | 39 | — | — |
| 0.1% Fe$_2$(SO$_4$)$_3$ + 1% NaClO$_3$ | 98 | 96 | 71 | 72 |

This example demonstrates that ferric salts can be used at very low levels to stabilize AI when an oxidant is used.

In summary of the above data, ferric salts have been discovered to be effective stabilizers for dilute solutions of AI. The stabilization is independent of the anion chosen, as long as the ferric salt is soluble in the system.

While this invention has been described in sufficient detail for those skilled in the art to be able to make and use it, various alternatives, modifications, and improvements should become apparent from the foregoing disclosure without departing from the spirit and scope of the invention.

I claim:

1. A method of preparing a stable, dilute solution of active ingredient consisting of 5-chloro-2-methyl-3-isothiazolone and, optionally, one or more additional 3-isothiazolone compounds, the concentration of said active ingredient in said solution being about 0.5 to 5% by weight based on solution, comprising introducing about 0.1 to 5% by weight based on said solution, of a water soluble, non-chelated ferric salt as the stabilizer and introducing sufficient acid to adjust said solution to a pH of less than about 1.5.

2. Method according to claim 1 wherein said acid is selected from the group consisting of hydrochloric acid, sulfuric acid, and nitric acid.

3. Method according to claim 1 wherein said salt is ferric sulfate and said acid is hydrochloric acid.

4. Composition comprising a dilute solution of (A) about 0.5 to 5.0 parts by weight of active ingredient consisting of 5-chloro-2-methyl-3-isothiazolone and optionally, one or more additional 3-isothiazolone compounds; (B) about 0.1 to 2.5 parts by weight of a stabilizing, water soluble, non-chelated ferric salt; (C) about 92 to 99 parts by weight of aqueous solvent; and (D) sufficient acid to maintain the solution pH at about less than 1.5.

5. Composition according to claim 4 wherein said acid is selected from the group consisting of hydrochloric acid, nitric acid, and sulfuric acid.

6. Composition according to claim 4 wherein (A) comprises about 1.5% by weight of said solution, and (B) comprises about 0.1 to about 2.5% by weight of said solution.

7. Composition according to claim 4 further comprising an oxidant selected from the group consisting of N-bromosuccinimide and sodium chlorate.

* * * * *